US010578591B2

(12) United States Patent
Okada et al.

(10) Patent No.: US 10,578,591 B2
(45) Date of Patent: Mar. 3, 2020

(54) GAS CHROMATOGRAPH

(71) Applicant: SHIMADZU CORPORATION, Kyoto (JP)

(72) Inventors: Masayuki Okada, Kyoto (JP); Yasunori Terai, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 514 days.

(21) Appl. No.: 13/761,180

(22) Filed: Feb. 7, 2013

(65) Prior Publication Data

US 2013/0247650 A1     Sep. 26, 2013

(30) Foreign Application Priority Data

Mar. 26, 2012 (JP) ................................ 2012-068928

(51) Int. Cl.
*G01N 30/02* (2006.01)
*G01N 30/32* (2006.01)
(52) U.S. Cl.
CPC ............. *G01N 30/02* (2013.01); *G01N 30/32* (2013.01); *G01N 2030/324* (2013.01)
(58) Field of Classification Search
CPC ............. G01N 30/02; G01N 2030/025; G01N 2030/324
USPC ............ 73/23.42; 137/513.3–513.7; 251/336
See application file for complete search history.

(56) References Cited

U.S. PATENT DOCUMENTS 3,794,077 A * 2/1974 Fanshier ............... F16K 15/063
137/513.3
4,976,750 A * 12/1990 Munari .................. G01N 30/32
95/19

5,524,473 A     6/1996 Haskell
5,545,252 A     8/1996 Hinshaw et al.
2002/0112707 A1 8/2002 Bircann et al.
(Continued)

FOREIGN PATENT DOCUMENTS

CN     2352785 Y     12/1999
GB     872259         7/1961
(Continued)

OTHER PUBLICATIONS

"First Office Action of China Counterpart Application", dated Jun. 17, 2014, with English translation thereof, p. 1-p. 13.
(Continued)

*Primary Examiner* — Daniel S Larkin
*Assistant Examiner* — Anthony W Megna Fuentes
(74) *Attorney, Agent, or Firm* — JCIPRNET

(57) ABSTRACT

A gas chromatograph for preventing leakage of carrier gas and secondary accident such as explosion is provided. A flow rate restricting valve having valve mechanism which mechanically restricts flow rate of carrier gas is disposed at the upstream side of sample inlet portion 1 of the carrier gas flow path 11 and apart from the flow rate control valve 6 which controls the flow rate of the carrier gas, which is inlet into sample inlet portion and analytical column according to signal from control unit 8. The excessive flow rate that is larger than the predetermined resulted from the leakage of carrier gas is mechanically restricted to a pre-set flow rate by using the flow rate restricting valve. The leakage of carrier gas e.g., helium and the secondary accident due to leakage of carrier gas e.g., hydrogen, are prevented.

2 Claims, 2 Drawing Sheets

(56) References Cited

U.S. PATENT DOCUMENTS

2005/0160790 A1* 7/2005 Tanaka .................. G01N 30/32
73/23.35
2005/0253103 A1 11/2005 Bente et al.

FOREIGN PATENT DOCUMENTS

| JP | H04160276 | 6/1992 |
| JP | H11258225 | 9/1999 |
| JP | H11311359 | 11/1999 |
| JP | 2000-019165 | 1/2000 |
| JP | 2009216394 | 9/2009 |
| SU | 710029 | 1/1980 |
| WO | 2010120486 | 10/2010 |

OTHER PUBLICATIONS

"Third Office Action of China Counterpart Application", dated Dec. 10, 2015, pp. 1-16, with English translation thereof.
"Office Action of Japan Counterpart Application," dated Apr. 21, 2015, p. 1-p. 3.
"Office Action of Japan Counterpart Application," dated Dec. 16, 2015, p. 1-p. 4.
"Office Action of Japan Counterpart Application," dated Jul. 26, 2016,with English translation thereof, p. 1-p. 4.
"Office Action of China Counterpart Application," dated Apr. 13, 2015, p. 1-p. 8.
Dung Liu,"Detection of Medicine Residual Solvents by Headspace Gas Chromatography",Chinese Master's These Full-text Database, Beijing University of Chinese Medicine, May 2007, with English abstract,pp. 1-82.
Shanghai Feikete Electrical Technology Co., Ltd.,"Instruction Manual of GS-101D Power System Dedicated Gas Chromatograph", Aug. 15, 2011,with English translation thereof, pp. 1-95.
"Office Action of China Counterpart Application," dated Aug. 9, 2016, p. 1-p. 6.
John V. Hinshaw, "GC Connections: An Alarming Situation", LCGC North America,vol. 20, No. 3, Mar. 1, 2002, pp. 276-279.
Matheson Tri-Gas, Inc.,"Safe Handling of Compressed Gases in the Laboratory and Plant",Dec. 31, 2011, pp. 1-16.
"Office Action of China Counterpart Application," dated May 27, 2017,with English translation thereof, p. 1-p. 27.
"Office Action of China Counterpart Application," with English translation thereof, dated Jan. 30, 2018, p. 1-p. 7.

* cited by examiner

GAS CHROMATOGRAPH

CROSS-REFERENCE TO RELATED APPLICATION

This application claims the priority benefit of Japan application serial no. 2012-068928, filed on Mar. 26, 2012. The entirety of the above-mentioned patent application is hereby incorporated by reference herein and made a part of this specification.

BACKGROUND OF THE INVENTION

1. Field of the Invention

The present invention generally relates to a gas chromatograph having a double safety structure for the leakage of carrier gas.

2. Description of Related Art

Inert gases such as helium, hydrogen, nitrogen, argon and the like are used as carrier gases for gas chromatographs, because of their conditions of inertness and low viscosity which can be set to analytical column.

Among the aforementioned gases, although nitrogen gas is a cheap and safe carrier gas, the analysis is time consuming due to the disadvantages of slow optimum linear speed and narrow optimum linear speed range. Although hydrogen gas is an ideal carrier gas due to the low cost, high optimum linear speed and broad optimum linear speed range, if safety is taken into account, using the hydrogen gas is generally and often avoided. Therefore, helium gas is often used due to the preferable safety and broad optimum linear speed range, and the hydrogen gas is used as a carrier gas in hydrogen flame ionization detector (FID).

However, in current years, since the price of helium gas has soared and become very expensive, if helium gas is used as the carrier gas, leakage of gas is wasteful and must be avoided. In addition, if hydrogen gas is used as the carrier gas, it is very dangerous because more than 4% of hydrogen in concentration in air due to leakage may cause an explosion; thus, adequate attention including an anti-leakage strategy is necessary.

On the other hand, in a conventional gas chromatograph, the carrier gas flow rate is an important factor for the repeatability (or reproducibility) of retention time and separation; in order to control the flow rate to be the optimum flow rate, a flow rate control valve is disposed in the carrier gas flow path, wherein the flow rate control valve is controlled according to the signal of flow rate sensor (referring to Japanese Patent Publication No. 2000-19165).

Accordingly, the carrier gas may leak because of the damage of an analytical column (capillary column), and failure and defect of the connection between analytical column and sample inlet portion, or between analytical column and detecting device. When the flow rate is an excessive flow rate, which is larger than the constant flow rate, though it is different from the original purpose, the flow rate is detected by the flow rate sensor. The carrier gas flow path is closed through the flow rate control valve based on the signal of the control unit and the flow rate is controlled (restricted) and the leakage of carrier gas is handled.

However, since the flow rate sensor, the flow rate control valve and the control unit for the control thereof are electromagnetically driven and controlled, when there is a failure or power failure in the electrical system (circuit), the conventional gas chromatograph becomes unable to actuate the flow rate sensor and the flow rate control valve. Consequently, the leakage of carrier gas cannot be prevented, and sufficient corresponding countermeasures for the waste due to the leakage of carrier gas and occurrence of secondary accident such as explosion cannot be achieved in the conventional gas chromatograph.

SUMMARY OF THE INVENTION

Accordingly, in order to solve the above problems, the present invention is directed to provide a gas chromatograph having a double safety structure capable of effectively preventing the carrier gas leakage, unnecessary loss of the expensive carrier gas (e.g., helium) due to the leakage and occurrence of secondary accident due to the dangerous carrier gas (e.g., hydrogen), even when a failure or power failure occurs in the flow rate sensor, the flow rate control valve and the electrical system of the control unit.

The present invention is directed to provide a gas chromatograph, wherein when a carrier gas filled in a gas bomb is inlet into a sample inlet portion and an analytical column, the gas chromatograph is adapted to control a flow rate by using a flow rate control valve disposed in a carrier gas flow path between the gas bomb and the sample inlet portion. The gas chromatograph includes a flow rate restricting valve having a valve mechanism and adapted to mechanically restrict the flow rate with respect to an excessive flow rate that is larger than a predetermined flow rate of the carrier gas. The flow rate restricting valve is apart from the flow rate control valve and disposed at an upstream side of the sample inlet portion of the carrier gas flow path.

According to an exemplary embodiment of the present invention, in the gas chromatograph, the flow rate restricting valve is adapted to restrict the flow rate with respect to an excessive flow rate that is larger than the predetermined flow rate of the carrier gas to a pre-set flow rate which is less than the predetermined flow rate.

According to an exemplary embodiment of the present invention, in the gas chromatograph, the flow rate restricting valve is adapted to close the carrier gas flow path and cut off the carrier gas flow with respect to the excessive flow rate which is larger than the predetermined flow rate of the carrier gas.

According to an exemplary embodiment of the present invention, in the gas chromatograph, the flow rate restricting valve is disposed between the flow rate control valve of the carrier gas flow path and the gas bomb.

According to an exemplary embodiment of the present invention, even though the carrier gas leaks due to damage of the analytical column (capillary column) and failure and defect of the connection between the analytical column and the sample inlet portion, or between the analytical column and detecting device, and there is failure or defect in the control unit which controls the flow rate sensor and the flow rate control valve with respect to the excessive flow rate which is larger than the predetermined flow rate of the carrier gas, the flow rate restricting valve having a valve mechanism capable of mechanically restricting the flow rate is disposed apart from the flow rate control valve and at the upstream side of the sample inlet portion of the carrier gas flow path, thus, the leakage of carrier gas, such as helium, can be effectively prevented. Moreover, the occurrence of secondary accident due to leakage of the carrier gas, such as hydrogen, can also be avoided.

Moreover, according to an exemplary embodiment of the present invention, since the flow rate restricting valve has a valve mechanism capable of restricting the flow rate with respect to the excessive flow rate that is larger than the predetermined flow rate of the carrier gas to a pre-set flow rate which is less than the predetermined flow rate, the occurrence of secondary accident due to leakage of the carrier gas, such as hydrogen, can be prevented. Further, the given carrier gas flow rate can be maintained, and the damage of analytical column because of the stationary phase of inner surface of analytical column being reacted with the external air flowing back to the analytical column through the detecting device can be avoided.

In addition, according to an exemplary embodiment of the present invention, since the flow rate restricting valve has a valve mechanism capable to close the carrier gas flow path and cut off the carrier gas flow with respect to the excessive flow rate that is larger than the predetermined flow rate of the carrier gas, any waste due to the leakage of an expensive carrier gas (helium) can be reduced.

Moreover, according to an exemplary embodiment of the present invention, since the flow rate restricting valve has a valve mechanism disposed between the flow rate control valve of the carrier gas flow path and the gas bomb, sufficient corresponding measures are capable not only for the failure of the electrical system of the flow rate sensor, the flow rate control valve and the control unit for the control thereof, but also for the leakage of carrier gas following the damage of the flow sensor and the flow rate control valve.

In light of the above, since the gas chromatograph of the present invention includes a safety mechanism controlled by the conventional electrical system and the double safety structure of the safety mechanism merely controlled by mechanical structure, the leakage of the expensive helium gas used as the carrier gas can be effectively prevented. Furthermore, occurrence of a secondary accident due to the leakage of hydrogen gas can be avoided, and the gas chromatograph user can engage in the analytical work safely and securely.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

First Embodiment

Figure 1:
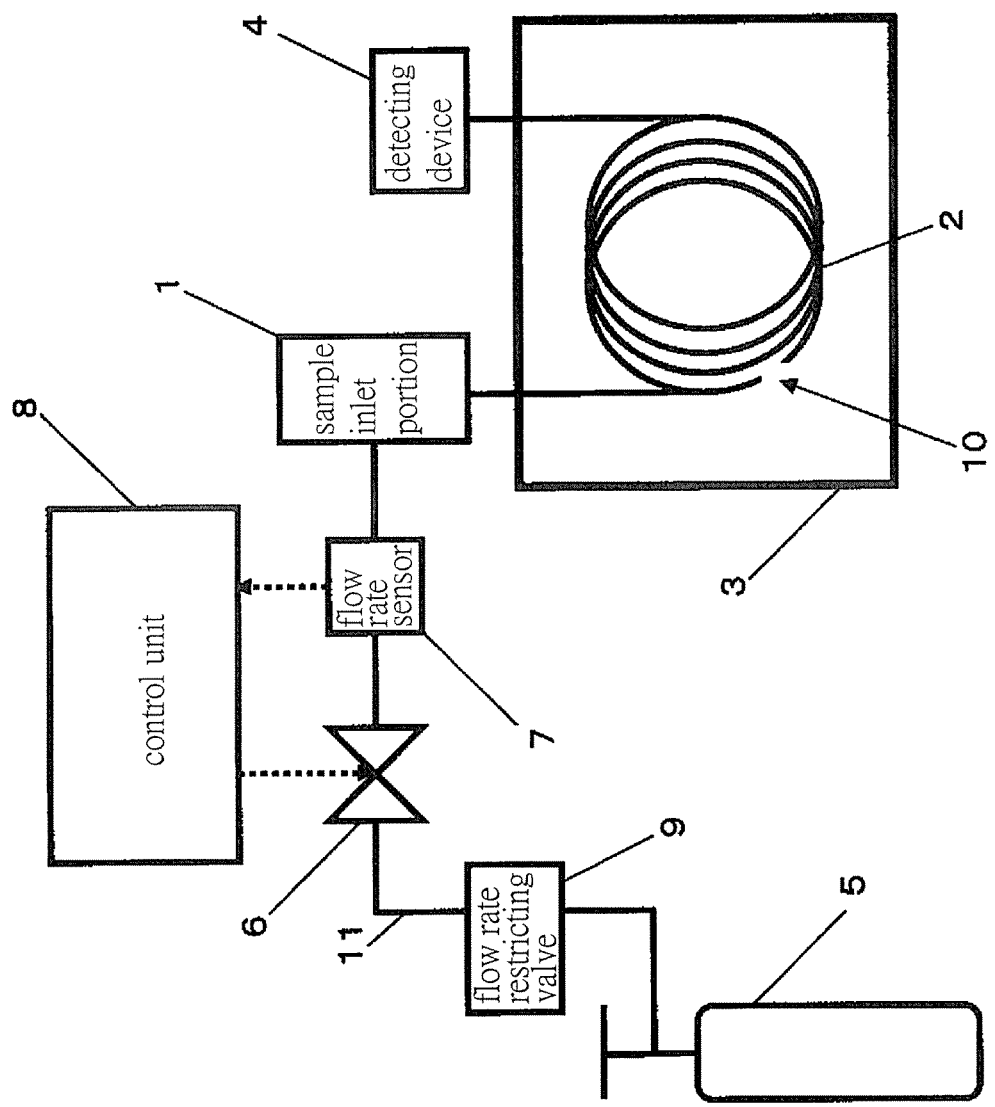
FIG. 1 is a schematic view of a gas chromatograph according to an exemplary embodiment of the present invention.

Reference will now be made in detail to the present preferred embodiments of the invention, examples of which are illustrated in the accompanying drawings. Wherever possible, the same reference counting numbers are used in the drawings and the description to refer to the same or like parts.

A gas chromatograph is described with drawings as an exemplary embodiment of the present invention.

FIG. 1 is a schematic view of a gas chromatograph according to an exemplary embodiment of the present invention. In FIG. 1, a sample inlet portion 1 including a sample vaporizing chamber (not shown), an analytical column 2 and a detecting device 4 are disposed in order in a carrier gas flow path 11. In general, the analytical column 2 uses a capillary column made of fused quartz (fused silica) and accommodated in an oven 3 surrounded by thermal insulating material, and the column temperature is controlled. The detecting device 4 is hydrogen flame ionization detector, for example.

The gas bomb 5 for providing the carrier gas is filled with hydrogen gas, for example. The flow rate control valve 6 and the flow rate sensor 7 which are electromagnetically driven and controlled are disposed at the upstream side of the sample inlet portion 1 of the carrier gas flow path 11. The flow rate control valve 6 provides an optimal flow rate of the carrier gas to the sample inlet portion 1 and the analytical column 2 based on the detected value of the flow rate sensor 7 and according to the control signal from the control unit 8 consisting of a CPU (central processing unit).

In accordance to the configuration of the gas chromatograph, a fluid sample is generally injected into the sample vaporizing chamber (not shown) of the sample inlet portion 1, during the analyzing process of the sample, after vaporized in vaporizing chamber by the high temperature, and inlet into the analytical column 2 accommodated in the oven 3 together with the carrier gas. Each composition of the sample is separated in the analytical column according to the chromatography principle, and the sample is then inlet into the detecting device 4 connected to the later part of the analytical column 2 and detected as a chromatogram.

Even not frequently, the carrier gas may leak due to the damage of analytical column 2 (capillary column), the failure and defect of the connection between the analytical column 2 and the sample inlet portion 1, or between the analytical column 2 and the detecting device 4. For instance, in the case of an on-column injection in which the fluid sample is directly inlet to the analytical column, since the syringe needle is inserted into the top of the analytical column 2, the analytical column 2 (capillary column) has a comparatively thin wall thickness and no strength and is easy to get damage. In FIG. 1, the damage portion 10 is schematically shown as the leakage portion, and in this condition, the leaked carrier gas may leak and flow to the oven 3 and the carrier gas flows in the carriage gas flow path 11 in an excessive flow rate.

In the gas chromatograph as shown in FIG. 1, in addition to the general structure of the conventional gas chromatograph, the flow rate restricting valve 9 is disposed between the gas bomb 5 and the flow rate control valve 6. The flow rate restricting valve 9 includes the valve mechanism which can mechanically actuate the flow rate with respect to the excessive flow rate which is larger than the predetermined flow rate of the carrier gas and restrict the carrier gas flow rate flowing through the carrier gas flow path 11.

The aforementioned valve mechanism of the flow rate restricting valve 9 includes the following functional aspects: (1) With respect to the excessive flow rate which is larger than the predetermined flow rate of the carrier gas, the flow rate of the carrier gas is restricted to a pre-set flow rate which is less than the predetermined flow rate. That is, the gas flow rate of the carrier is allowed to circulate in a given carrier gas flow rate.

(2) With respect to the excessive flow rate which is larger than the predetermined flow rate of the carrier gas, the carrier gas flow path 11 is closed and the carrier gas flow is cut off.

Any of the functions of the valve mechanism of the flow rate restricting valve 9 can be appropriately selected according to the type of carrier gas and the main purpose of the leakage prevention.

If the carrier gas flow path 11 is closed and the carrier gas flow is completely cut off, any waste due to the leakage of the expensive carrier gas can be eliminated. Moreover, if the dangerous hydrogen gas is used as the carrier gas, the occurrence of a secondary accident, such as explosion, due to leakage can be prevented.

On the other hand, if the carrier gas flow is completely cut off, the stationary phase of the inner surface of the analytical column 2 being reacted (oxidized) with the external air flowing back to the analytical column 2 through the detecting device 4 may deteriorate the analytical column 2.

Herein, as for the valve function of the flow rate restricting valve 9, without completely cutting off the carrier gas flow, the carrier gas flow is generally restricted to a pre-set flow rate which is less than the predetermined flow rate. Further, even though the flow rate is small, the carrier gas flow is maintained. Although there is unnecessary loss due to the leakage when the expensive helium gas is used as the carrier gas, sufficiently considering the condition of the explosion limit (the concentration of hydrogen in the air is 4%) due to leakage is possible, thus the flow rate restricting valve 9 can also cope with the use of hydrogen gas. Moreover, the air inlet to the analytical column 2 from the outside can also be prevented and the damage of analytical column 2 can further be avoided.

Figure 2:
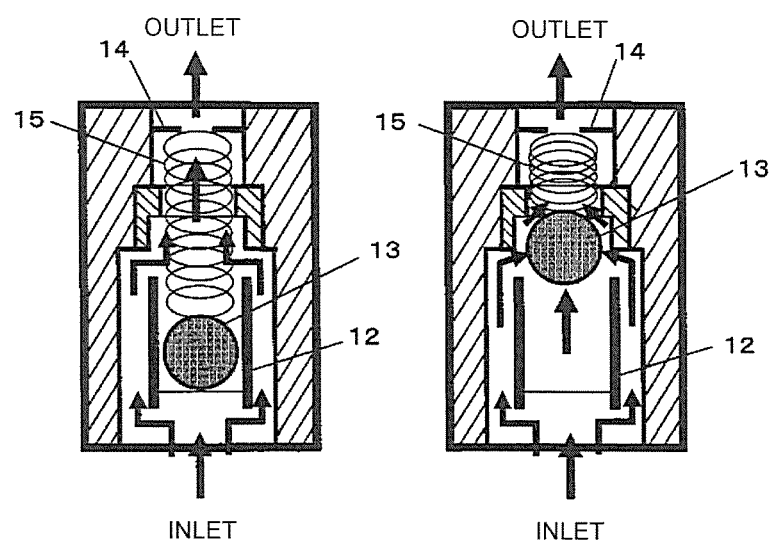
FIG. 2A schematically shows that the flow rate restricting valve of the gas chromatograph is in a normal condition.
FIG. 2B schematically shows that the flow rate restricting valve of the gas chromatograph is in an operating condition.

The flow rate restricting valve 9 is schematically shown in FIG. 2A and FIG. 2B, wherein FIG. 2A illustrates the normal condition and FIG. 2B illustrates the operating condition.

In a normal condition as shown in FIG. 2A, the ball 13 disposed in the cylinder 12 is stopped in the cylinder 12 due to its weight and the elastic force of the spring 15 disposed between the ball 13 and the stopper 14. When the carrier gas, at the excessive flow rate that is larger than the predetermined flow rate, flows through the ball 13 due to the leakage of carrier gas, namely in the operating condition as shown in FIG. 2B, the ball 13 resists the ball's weight and the elastic force of the spring 15 and rises to the outlet and is stopped where it is balanced, and the flow rate of the carrier gas is restricted to flow only in a pre-set flow rate which is less than the predetermined flow rate. Namely, without closing the carrier gas flow path 11 and without completely cutting off the carrier gas flow, the carrier gas flow rate is allowed to flow in the pre-set flow rate which is less than the predetermined flow rate. How much the carrier gas flow rate is allowed to flow can be appropriately set by adjusting the elastic force of the spring 15.

Certainly, instead of the elastic force of the spring, the structure in which the ball uses self-weight for balancing can also be used.

For instance, in the "capillary gas chromatograph GC-2010Plus" manufactured by SHIMADZU CORPORATION, the flow rate restricting valve 9 that restricts (allows) the carrier gas flow rate is set with the condition that more than a carrier gas at a flow rate of about 750 ml/min is not allowed to flow in the carrier gas flow path 11 including the analytical column 2. In the case that the hydrogen is used as the carrier gas, if the carrier gas flow rate is lower than about 750 ml/min, even if hydrogen leaks from the damage portion 10 of the analytical column 2 and fills up the oven 3, the concentration of the hydrogen gas does not exceed the explosion limit therefore, i.e., 4%. Since the thermal insulating material surrounding the oven 3 is permeable and there is also a slight clearance though the door is an air tight structure, unless the excessive flow rate which is over about 750 ml/min, the concentration of the hydrogen gas does not reach the explosion limit, i.e., 4%, of the hydrogen gas. Certainly, the deterioration of the analytical column 2 is not caused.

In the gas chromatograph of the exemplary embodiment shown in FIG. 1, the flow rate restricting valve 9 is disposed between the gas bomb 5 and the flow rate control valve 6. In this case, although it is preferable that the leakage of carrier gas due to the damage of flow rate control valve 6 can be handled by corresponding measures, at least in the present invention, if the flow rate restricting valve 9 is disposed at an upstream side of the sample inlet portion 1, the mentioned function can also be achieved.

Furthermore, the flow rate restricting valve 9 which actuates merely by mechanical structure can be various flow rate restricting valves or flow rate control valves that are commercially available and consisting of the flow-rate-adjustable structure in which the flow rate can be restricted and set as required, and the present invention is not limited to a specified structure.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A gas chromatograph, wherein when a carrier gas filled in a gas bomb is inlet into a sample inlet portion and an analytical column, the gas chromatograph is configured to control a flow rate of the carrier gas, the gas chromatograph is consisting of: a flow rate control valve electromagnetically controlled, disposed in a carrier gas flow path between the gas bomb and the sample inlet portion, and configured to restrict the flow rate with respect to an excessive flow rate that is larger than a predetermined flow rate of the carrier gas, a flow rate restricting valve disposed between the flow rate control valve of the carrier gas flow path and the gas bomb, apart from the flow rate control valve, and disposed at an upstream side of the sample inlet portion of the carrier gas flow path, wherein the flow rate restricting valve has a valve mechanism that is configured to mechanically restrict the flow rate with respect to the excessive flow rate that is larger than the predetermined flow rate of the carrier gas and allows the carrier gas to circulate in a given carrier gas flow rate, and no gas flow path is joined to the carrier gas flow path through which the flow rate restricting valve and the flow rate control valve are connected, and in the carrier gas flow path between the gas bomb and the flow rate control valve, only the flow rate restricting valve is disposed, so as to configure a double safety structure consisted of the flow rate restricting valve and the flow rate control valve in series from the upstream side, wherein the valve mechanism does not actuate when the flow rate of the carrier gas is less than the predetermined flow rate, restricts the flow rate of the carrier gas to a pre-set flow rate which is less than the predetermined flow rate, when the flow rate of the carrier gas flows in the excessive flow rate that is larger than the predetermined flow rate, and is configured to adjust an allowed flow rate of the carrier gas, wherein an air inlet to the analytical column from outside is prevented.

2. The gas chromatograph according to claim 1, wherein the flow rate restricting valve having the valve mechanism is configured to close the carrier gas flow path and cut off the carrier gas flow rate with respect to the excessive flow rate that is larger than the predetermined flow rate of the carrier gas.

\* \* \* \* \*